(12) United States Patent
Benke et al.

(10) Patent No.: US 7,863,482 B2
(45) Date of Patent: Jan. 4, 2011

(54) PROCESS FOR PURIFYING MESOTRIONE

(75) Inventors: Alan Henry Benke, Bucks, AL (US); Julie Marie Wichert, Bucks, AL (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/598,993

(22) PCT Filed: Mar. 3, 2005

(86) PCT No.: PCT/EP2005/002230

§ 371 (c)(1),
(2), (4) Date: Jul. 3, 2007

(87) PCT Pub. No.: WO2005/092846

PCT Pub. Date: Oct. 6, 2005

(65) Prior Publication Data

US 2008/0039661 A1  Feb. 14, 2008

(30) Foreign Application Priority Data

Mar. 26, 2004 (GB) ................... 0406894.6

(51) Int. Cl.
*C07C 315/00* (2006.01)
(52) U.S. Cl. ........................................ 562/429; 568/30
(58) Field of Classification Search .................... 568/30, 568/309, 308

See application file for complete search history.

(56) References Cited

U.S. PATENT DOCUMENTS

| | | | |
|---|---|---|---|
| 4,695,673 A | 9/1987 | Heather et al. | |
| 4,937,386 A * | 6/1990 | Ueda et al. ................... | 504/348 |
| 5,085,688 A * | 2/1992 | Michaely et al. ............ | 504/348 |
| 6,218,579 B1 | 4/2001 | Jones et al. | |
| 7,285,678 B2 * | 10/2007 | Javdani et al. ............... | 562/429 |

* cited by examiner

*Primary Examiner*—Daniel M Sullivan
*Assistant Examiner*—Chukwuma O Nwaonicha
(74) *Attorney, Agent, or Firm*—William A. Teoli, Jr.

(57) ABSTRACT

A method for reducing the cyanide levels in a mesotrione sample, said method comprising: (i) taking an aqueous solution of the mesotrione sample in an aqueous solvent, (ii) adjusting the pH of said aqueous solution to a value of 9.5 or higher, and (iii) crystallising the mesotrione out of solution is disclosed.

8 Claims, No Drawings

PROCESS FOR PURIFYING MESOTRIONE

This application is a 371 of International Application No, PCT/EP2005/002230 filed Mar. 3, 2005, which claims priority to GB 0406894,6 filed Mar. 26, 2004, the contents of which are incorporated herein by reference.

The present invention relates to a novel method for reducing the cyanide content of a mesotrione sample.

Mesotrione (2-(2'-nitro-4'-methylsulphonyl benzoyl)-1,3-cyclohexanedione) is a selective corn herbicide and has the structure of formula (I)

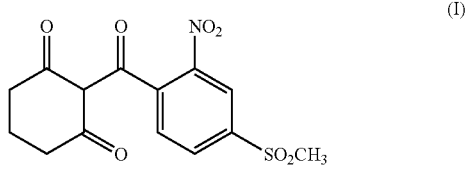

Mesotrione is prepared by reacting 2-nitro-4-methylsulphonyl benzoyl chloride with cyclohexanedione to give the enol ester, followed by a rearrangement reaction to give mesotrione, as shown in the following reaction scheme:

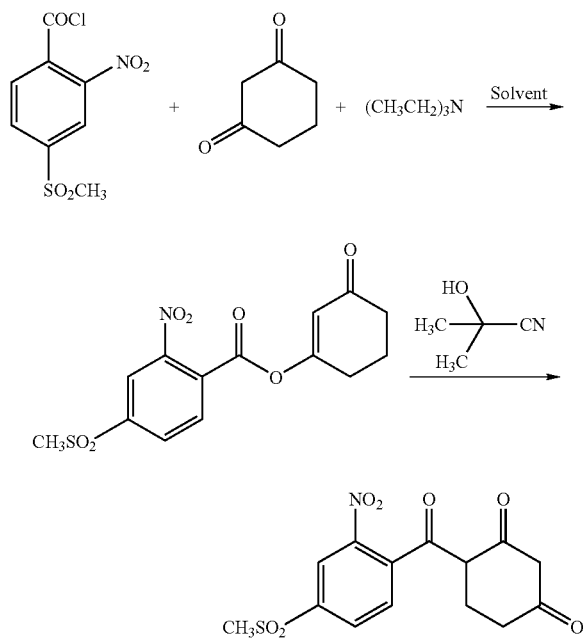

2-Nitro-4-methylsulphonyl benzoyl chloride is prepared from the corresponding benzoic acid, which in turn is prepared by oxidation of 2-nitro-4-methylsulphonyl toluene. More details on the preparative route may be found in U.S. Pat. No. 4,695,673.

During the rearrangement process, the mesotrione sample is contaminated with cyanide residues from the acetone cyanohydrin catalyst. It is therefore an object of the present invention to provide a simple, but effective method for reducing the level of cyanide residues in the mesotrione sample to an acceptable level.

It has surprisingly been found that adjusting the pH of a mesotrione sample in aqueous solution has a significant impact on the resulting cyanide levels.

Accordingly the present invention provides a method for reducing the cyanide levels in a mesotrione sample, said method comprising:

(i) taking an aqueous solution of the mesotrione sample in an aqueous solvent, (ii) adjusting the pH of said aqueous solution to a value of 9.5 or higher, and (iii) crystallising the mesotrione out of solution.

In one embodiment of the invention, the mesotrione sample has previously been isolated, and the aqueous solution is formed by dissolving the isolated sample in an aqueous solvent.

In a second embodiment of the invention, the mesotrione sample has not previously been isolated and remains dissolved in the aqueous solvent used in the condensation/rearrangement reaction described above.

The aqueous solvent may be selected from the group consisting of water and a water soluble solvent, such as acetonitrile, triethylamine, methanol, ethanol, acetone. Preferably, the aqueous solvent is water. The mesotrione sample is suitably dissolved in the aqueous solvent to give a solution concentration of from 1% to 30%, suitably from 5% to 15%, and preferably from 8% to 11%.

Suitably, the pH of the aqueous solution is raised to a pH of at least 11, and preferably at least 11.5. Suitably, the aqueous mesotrione sample is held at a pH of at least 9.5 for at least 5 minutes, suitably at least 15 minutes and preferably at least 30 minutes.

Suitably, the temperature of the aqueous solution should not be greater than 30° C.

The crystallisation is carried out according to standard laboratory procedures. For example, for a batch crystallisation, the final pH is adjusted from its starting value of 9.5 or higher to pH 2.5 by charging hydrochloric acid to the crystalliser. The hydrochloric acid should be charged in a manner to ensure adequate mixing. The crystallisation process may also be carried out as a semi-batch or continuous process. The crystallisation step may also include a nitrogen-sparging step, wherein nitrogen is bubbled through the crystallisation vessel in a continuous fashion and sent to a scrubber.

The method of the invention may further include a distillation step to remove solvents when the mesotrione sample has not previously been isolated (i.e. the second embodiment of the invention). The distillation step may be carried out either before or after adjusting the pH to 9.5 or higher. The distillation step is suitably carried out using a sufficient amount of steam to remove the solvents from the aqueous solution.

Suitably, the method of the invention reduces the cyanide levels in the mesotrione sample to 150 ppm or less, more suitably 100 ppm or less and preferably 50 ppm or less.

The invention will now be described further with reference to the following examples, which are illustrative but not limiting of the invention.

EXAMPLE 1

Wet paste mesotrione that was high in total CN was subjected to different treatments in an effort to reduce the total CN content. The results are shown in Table 1.

TABLE 1

| Example No. | Treatment | Original Cyanide Content (PPM) | Cyanide Content after Treatment (PPM) | % reduction in Cyanide content |
|---|---|---|---|---|
| 1A | Mesotrione was placed in water to make an aqueous solution at a concentration of ~10%, pH was adjusted to >13, ACN was charged, and the mixture was then batch crystallised following standard lab procedures. | 546 | 15 | 97% |
| 1B | Mesotrione was placed in water to make an aqueous solution at a concentration of ~10%, pH was adjusted to 11.3, ACN was charged, and the mixture was batch crystallised following standard lab procedures. | 1114 | 557 | 50% |
| 1C | Mesotrione was placed in water to make an aqueous solution at a concentration of ~10%, pH was adjusted to >13, ACN was charged, and the mixture was batch crystallised following standard lab procedures. | 1114 | 50 | 96% |
| 1D | Mesotrione was placed in water to make an aqueous solution at a concentration of ~10%, pH was adjusted to 11.3, ACN was charged, and the mixture was batch crystallised following standard lab procedures. | 690 | 150 | 78% |
| 1E | Mesotrione was placed in water to make an aqueous solution at a concentration of ~10%, pH was adjusted to 12-13, ACN was charged, and the mixture was batch crystallised following standard lab procedures. | 690 | 170 | 75% |

EXAMPLE 2

Mesotrione was crystallised from samples taken from the plant during the solvent distillation. Samples were taken from the same batch after both 4500 lbs steam (distillation not finished) and 5000 lbs steam (distillation finished) had been used during the distillation process. The pH of the sample was adjusted and the samples were crystallised via standard lab procedures. Total CN content was measured by titration of the wet paste. The results are given in Table 2.

TABLE 2

| Example No. | Distillation Complete? | Starting pH of crystallisation | Total CN of wet paste (PPM) |
|---|---|---|---|
| 2A | No | 9.5 | 278 |
| 2B | Yes | 9.5 | 651 |
| 2C | No | 11.1 | 120 |
| 2D | Yes | 11.1 | 26 |
| 2E | No | 12.8 | 121 |
| 2F | Yes | 12.8 | 20 |

EXAMPLE 3

Mesotrione was crystallised from samples taken from the plant during the solvent distillation. The effects of varying the starting pH of the crystallisation and purging the headspace of the crystallisation vessel with nitrogen were looked at. Samples were taken from the same batch after both 4500 lbs steam (distillation not finished) and 5045 lbs steam (distillation finished) has been used during the distillation. The pH of the sample was adjusted and the samples were crystallised via standard lab procedures. Total CN was measured by titration of the wet paste or filtrate. The results are shown in table 3.

TABLE 3

| Example No. | Distillation Complete | Starting pH of crystallisation | $N_2$ purge? | Total CN content of wet paste (PPM) | % reduction in cyanide content from control |
|---|---|---|---|---|---|
| 3A | No | 5.2 | No | 311 | Control |
| 3B | Yes | 5.2 | No | 236 | Control |
| 3C | No | 9.5 | No | 91 | 70 |
| 3D | Yes | 9.5 | No | 63 | 74 |
| 3E | No | 11.0 | No | 20 | 94 |
| 3F | Yes | 11.0 | No | 50 | 79 |
| 3G | No | 13 | No | 15 | 95 |
| 3H | Yes | 13 | No | 56 | 76 |
| 3I | No | 5.2 | Yes | 294 | Control |
| 3J | No | 11.0 | Yes | 46 | 85 |
| 3K | No | 11.3 | Yes | 15 | 95 |

EXAMPLE 4

This example looks at the cyanide content of mesotrione crystallised from different feed pH in a continuous crystallisation. The results are shown in Table 4.

TABLE 4

| Sample | pH of feed to crystalliser | Total CN (ppm) | % Reduction in Cyanide Content from Control |
|---|---|---|---|
| 7$^{th}$ (final) sample from crystalliser | 5.0 | 217 | Control |
| 7$^{th}$ (final) sample from crystalliser | 5.0 | 181 | Control |
| 7$^{th}$ (final) sample from crystalliser | 11 | 15 | 92-93 |
| Final sample from crystalliser | 11 | 15 | 92-93 |
| Final sample from crystalliser | 11 | 15 | 92-93 |
| Final sample from crystalliser | 9.5 | 15 | 92-93 |

EXAMPLE 5

Mesotrione was produced from the acid chloride by a standard condensation/rearrangement reaction. After the condensation/rearrangement reaction, water was added and the pH was adjusted to >11 and held for ½ hour. The pH was then adjusted to ~5, the mixture distilled and then batch crystallised from either pH 5 or 9.5. The results are shown in Table 5.

TABLE 5

| Example No. | pH held at after condensation/ rearrangement reaction | Starting pH of crystallisation | Total CN in mesotrione (ppm) |
|---|---|---|---|
| 5A | 11.9 | 5.0 | 15 |
| 5B | 11.3 | 9.5 | 40 |

EXAMPLE 6

A large sample of mesotrione was obtained at the end of the distillation. This sample was divided into aliquots which were adjusted to a pH >11. A series of batch samples were made up and held agitated at the given pH for the amount of time specified in the table before being quickly adjusted to pH 2.4, filtered, washed and submitted for total cyanide analysis. The results are shown in Table 6.

TABLE 6

| Example No. | Starting pH | Time kept at starting pH (min) | Total CN of mesotrione (ppm) |
|---|---|---|---|
| 6A | 11.6 | 0 | 111 |
| 6B | 11.3 | 5 | 76 |
| 6C | 11.5 | 10 | 72 |
| 6D | 11.6 | 15 | 73 |
| 6E | 11.5 | 20 | 55 |
| 6F | 11.5 | 25 | 72 |
| 6G | 11.4 | 30 | 76 |
| 6H | 11.7 | 60 | 15 |
| 6I | 12.3 | 90 | 15 |

The invention claimed is:

1. A method for reducing the cyanide levels in a mesotrione sample, said method comprising:
    (i) taking an aqueous solution of the mesotrione sample in an aqueous solvent,
    (ii) adjusting the pH of said aqueous solution to a value of 9.5 or higher, and
    (iii) crystallising the mesotrione out of solution.

2. The method of claim 1, wherein the mesotrione sample has previously been isolated and is redissolved in an aqueous solvent.

3. The method of claim 1, wherein the mesotrione sample has not previously been isolated and is already present as an aqueous solution in an aqueous solvent.

4. The method of claim 3, which further includes a distillation step.

5. The method of claim 4, wherein the distillation step is carried out prior to adjusting the pH of the aqueous solution to a value of 9.5 or higher.

6. The method of claim 4, wherein the distillation step is carried out after adjusting the pH of the aqueous solution to a value of 9.5 or higher.

7. The method according to claim 1, wherein the crystallisation step also includes a nitrogen sparging step.

8. A method according to any one of claim 1, wherein the cyanide levels in the mesotrione sample are reduced to 150 ppm or less.

* * * * *